United States Patent [19]

Staiger et al.

[11] Patent Number: 4,731,466
[45] Date of Patent: Mar. 15, 1988

[54] HYDROXYPHENYL- AND HYDROXYPHENOXYALKANOIC ACID IODOPROPARGYL ESTERS

[75] Inventors: Gerhard Staiger, Altoetting; Peter Kinzel, Feldkirchen, both of Fed. Rep. of Germany

[73] Assignee: The Dow Chemical Company, Midland, Mich.

[21] Appl. No.: 44,164

[22] Filed: Apr. 30, 1987

[30] Foreign Application Priority Data

May 2, 1986 [DE] Fed. Rep. of Germany ....... 3614836

[51] Int. Cl.$^4$ .............................................. C07C 69/76
[52] U.S. Cl. ...................... 560/75; 560/61; 560/62; 560/23; 560/11; 560/21
[58] Field of Search ....................... 560/75, 61, 62, 23, 560/11; 514/533, 534

[56] References Cited

U.S. PATENT DOCUMENTS 4,259,350  3/1981  Morisawa et al. ................... 514/543

FOREIGN PATENT DOCUMENTS 2910220  9/1979  Fed. Rep. of Germany .
122727   9/1979  Japan .
43205    4/1981  Japan .

Primary Examiner—Paul J. Killos

[57] ABSTRACT

The invention concerns compounds having the formula

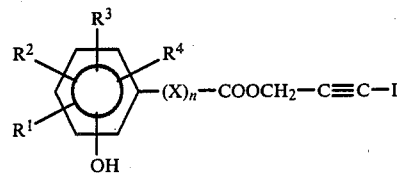

wherein
$R^1$, $R^2$, $R^3$, $R^4$ can mean identical or different radicals in any desired position on the benzene ring, namely fluoro, chloro, bromo, iodo, cyano, or nitro radicals, alkyl radicals having from 1 to 4 carbon atoms, cyclo alkyl radicals having from 3 to 7 carbon atoms, phenyl, phenylsulfonyl and phenoxy radicals and hydrogen;
n can mean a number with the value of 1 or 2 and
x can mean $CH_2$, and where $n=1$, $O—CH_2$ as well.
The named componds show efficiency as fungicides.

8 Claims, No Drawings

HYDROXYPHENYL- AND HYDROXYPHENOXYALKANOIC ACID IODOPROPARGYL ESTERS

The invention concerns new compounds, namely hydroxyphenyl- and hydroxyphenoxyalkanoic acid iodopropargyl esters and their use as active ingredients in fungicides.

From ZA No. 835,278 (published on Apr. 25, 1984, F. Maurer et al., Bayer AG) it is known that iodopropargyl esters can be prepared from dicarboxylic acids, and that these esters can be used as active ingredients in plant protective agents. In U.S. Pat. No. 4,259,350 (issued on Mar. 31, 1981, Y. Morisawa et al., Sankyo Company Ltd.) unsubstituted and ring-substituted benzoic acid iodopropargyl esters and their effect against termites are claimed.

The present invention has compounds having the following formulas as its subject:

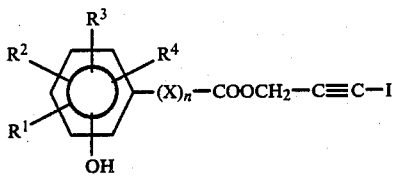

(I)

where $R^1$, $R^2$, $R^3$, $R^4$ are identical or different radicals, namely fluoro-, chloro-, bromo-, iodo, cyano- or nitro radicals, alkyl radicals having from 1 to 4 carbon atoms, cyclo alkyl radicals having from 3 to 7 carbon atoms, the phenylsulfonyl-, phenyl, phenoxy radical or hydrogen;

n can mean 1 or 2 and

X can mean $CH_2$ and, if n=1, also $O-CH_2$.

The preferred radicals $R^1$ and $R^2$ are nitro groups, hydrogen atoms and chlorine atoms. The preferred radicals $R^3$ and $R^4$ are hydrogen atoms.

The compounds of the above formula are distinguished by outstanding effectiveness against a plurality of phytopathogenic fungi.

Examples of the iodopropargyl esters which are especially preferred according to the invention, namely unsubstituted and ring-substituted hydroxyphenylacetic acid iodopropargyl esters, hydroxyphenoxyacetic acid iodopropargyl esters and beta-hydroxyphenylpropionic acid iodopropargyl esters are the following compounds:

(1) hydroxyphenylacetic acid iodopropargyl esters:
(a) (2-hydroxyphenyl)acetic acid iodopropargyl ester
(b) (3-hydroxyphenyl)acetic acid iodopropargyl ester
(c) (4-hydroxyphenyl)acetic acid iodopropargyl ester
(d) (2-hydroxy-5-nitrophenyl)acetic acid iodopropargyl ester
(e) (2-hydroxy-5-chlorophenyl)acetic acid iodopropargyl ester
(f) (2-hydroxy-3,5-dinitrophenyl)acetic acid iodopropargyl ester
(g) (3-hydroxy-4-nitrophenyl)acetic acid iodopropargyl ester (2) hydroxyphenoxyacetic acid iodopropargyl esters:
(a) (2-hydroxyphenoxy)acetic acid iodopropargyl ester
(b) (2-hydroxy-5-nitrophenoxy)acetic acid iodopropargyl ester
(c) (2-hydroxy-3,5-dinitrophenoxy)acetic acid iodopropargyl ester (3) beta-(hydroxyphenyl)propionic acid iodopropargyl ester:
(a) beta-(2-hydroxyphenyl)propionic acid iodopropargyl ester
(b) beta-(2-hydroxy-3-nitrophenyl)propionic acid iodopropargyl ester
(c) beta-(2-hydroxy-5-nitrophenyl)propionic acid iodopropargyl ester
(d) beta-(2-hydroxy-5-chlorophenyl)propionic acid iodopropargyl ester
(e) beta-(2-hydroxy-3,5-dinitrophenyl)propionic acid iodopropargyl ester
(f) beta-(3-hydroxyphenyl)propionic acid iodopropargyl ester.

Of the above named compound titles, the following concepts correspond to the IUPAC nomenclature below:

acetic acid=ethanoic acid
propionic acid=propanoic acid
iodopropargyl-=3-iodo-2-propynyl.

The inventive unsubstituted or ring-substituted hydroxyphenyl- or hydroxyphenoxyalkanoic acid iodopropargyl esters are accessible by the esterification of the corresponding acids or of their derivatives with $I-C\equiv C-CH_2OH$ (3-iodo-2-propyne-1-ol or 3-hydroxy-1-iodo-1-propyne). 3-iodo-2-propyne-1-ol and its preparation are described for example in U.S. Pat. No. 3,075,938 (issued on Jan. 23, 1963, R. L. Johnson, The Dow Chemical Company).

As the initial compounds in the process for the preparation of the iodopropargyl esters according to the invention, apart from 3-iodo-2-propyne-1-ol as the first component, the compounds of the following formula serve as the second component respectively:

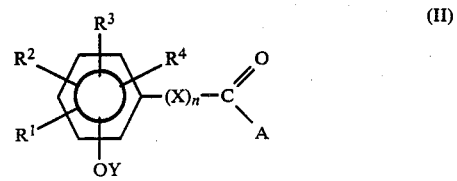

(II)

wherein $R^1$, $R^2$, $R^3$, $R^4$, X and n have the meanings given above for formula (I) and A represents chlorine, bromine, iodine, an acyloxy group having from 1 to 18 carbon atoms, an alkoxycarbonyloxy group having from 2 to 18 carbon atoms, a phenoxy radical which is optionally substituted by nitro-, cyano-, trihalogenmethyl and/or $C_1-C_8$ acyl groups and/or halogen, and Y represents an acyl radical having from 1 to 10 carbon atoms. Preferred examples of R are chlorine, bromine, the acetyl group, the 2,2-dimethylpropionyl-, the benzoyloxymethoxycarbonyloxy-, ethoxycarbonyloxy-, 2,4-dinitrophenoxy- and 4-nitrophenoxy groups.

Preferred examples of Y are the acetyl and benzoyl groups.

If the iodopropargyl esters to be prepared according to the invention are unsubstituted or ring-substituted 2-hydroxyphenyl- or 2-hydroxyphenoxyalkanoic acid iodopropargyl esters having the formula

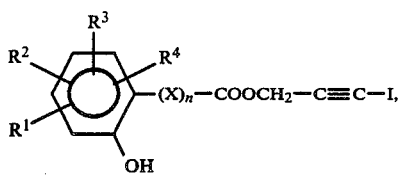

instead of an initial compound of formula (II), a lactone having the formula

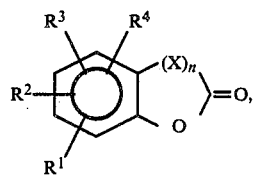

can be and preferably is used, where $R^1$, $R^2$, $R^3$, $R^4$, X and n have respectively the same meanings as in formula (III).

The reaction of the compounds of formula (II) or (IV) with 3-iodo-2-propyne-1-ol is preferably carried out in the presence of an acidic or basic catalyst. Especially preferred are basic catalysts such as lithium hydroxide, lithium carbonate, sodium hydroxide, sodium carbonate, calcium oxide, calcium carbonate, dolomite, magnesium oxide, magnesium carbonate, potassium hydroxide, potassium carbonate, primary, secondary and tertiary amines. Of these basic catalysts, tertiary organic amines are preferred in particular, such as for example pyridine, N,N-dimethylcyclohexylamine, trimethylamine, triethylamine, N-methylmorpholine, 4-(N,N-dimethylamino)-pyridine, N-methylpiperidine, ethyldiisopropylamine, 2-, 4-, 6-trimethylpyridine (sym. collodine) and diazadicyclo-[2,2,2]-octane.

The initial substances of formulae (II) and (IV) can partially be obtained on the market. For example the initial compounds or their immediate precursors are obtainable from Aldrich-Europe, B-2340 Beerse, Belgium, for the following of the above named compounds:
1(a) 2-coumaranone, i.e. 2-hydroxyphenylacetic acid
1(b) 3-hydroxyphenylacetic acid
1(c) 4-hydroxyphenylacetic acid
1(g) 3-hydroxy-4-nitrophenylacetic acid
3(a) 3,4-dihydrocoumarin
3(f) 3-hydroxyphenylpropionic acid The initial substances for 1(d)–(f) and 3(b)–(e) can be obtained by nitration or chlorination from 2-coumaranone or from 3,4-dihydrocoumarin.

Other or additional electrophile substitution reactions, such as sulfonation, alkylation according to Friedel-Crafts, cyanation, bromination, fluoration, iodination, hydroxylation (which can be carried out after etherification of the OH group) lead to further initial substances of the compounds according to the invention. All these reactions have long been adequately known. A survey of these reactions is given for example by Houben-Weyl, Methoden der organischen Chemie, 4th edition, volume 5/2b, pages 508 to 527, Georg Thieme Verlag, Stuttgart, New York 1981. Basic text books for organic chemistry, for example, J. B. Hendrickson, D. J. Cram and G. S. Hammond, Organic Chemistry, 3rd edition, McGraw-Hill Kogakusha Ltd., Tokyo 1970, pages 651 to 687 report on the reagents to be used as well as on the directing influence of the existing first substituents on aromatics. Thus, for example, when using concentrated nitric acid or, if a stronger reagent is necessary with a mixture of equal parts by volume of concentrated nitric acid and concentrated sulphuric acid, the nitration is carried out. The chlorination can be performed by the introduction of chlorine gas with catalysis of $AlCl_3$, $FeCl_3$, iron or iodine.

Suitable solvents for these reactions include inter alia dichloromethane, trichloromethane, tetrachloromethane and dioxan.

The initial substances for the hydroxyphenoxyacetic acid iodopropargyl esters ($X=-O-CH_2-$ and $n=1$ in formula (I)) can be prepared from the corresponding dihydroxybenzenes, for example, from 1,2-dihydroxybenzene (catechol) 1,3-dihydroxy-benzene (resorcinol) and 1,4-dihydroxybenzene (hydroquinone); the former substance can be obtained form E. Merck, D-6100 Darmstadt, and the two latter substances from Janssen Chimica, D-4054 Nettetal 2.

The named dihydroxybenzenes can be reacted in the manner known per se with chloroacetic acid (esters) to form hydroxyphenoxyacetic acids (esters) (Organikum, 13th edition 1974, page 226, VEB Deutscher Verlag der Wissenschaften, Berlin). Particularly advantageous is the reaction of unsubstituted or ring-substituted 1,2-dihydroxybenzenes with chloroacetic acid chloride. As is explained in Example 3 of the present application, the reaction leads primarily to the corresponding (2-hydroxyphenyl)chloroacetic acid ester. This can be cyclicized to form unsubstituted or corresponding ring-substituted 3H-benzo-1,4-dioxin-2-one, preferably in the presence of a base, such as, for example, sodium hydride.

The 3H-benzo-1,4-dioxin-2-one derivatives which are thus obtained can all contain the desired radicals $R^1$, $R^2$, $R^3$ and $R^4$ in the end product. But more advantageously one or more of these radicals can also be introduced into the unsubstituted or aromatically substituted 3H-benzo-1,4-dioxin-2-one. The reaction conditions correspond essentially to the conditions listed above for the 2-coumaranone or the 3,4-dihydrocoumarin. The cyclization of the hydroxy acids which then arise into lactone, i.e. the reaction of the unsubstituted or ring-substituted 2-hydroxyphenylacetic acid, 2-hydroxyphenoxyacetic acid or 2-hydroxyphenylpropionic acid (derivatives) to form the corresponding 2-coumaranones, 3H-benzo-1,4-dioxin-2-ones or 3,4-dihydrocoumarin is preferably carried out at pressures from 0.09 to 0.11 MPa (abs). As for the reaction temperatures, those from 0° C. to 130° C., especially from 15° to 100° C., are preferred. For preference the cyclization is carried out in the presence of one or more inert and largely anhydrous solvents. The solvent can contain a separating agent which facilitates the separation by distillation of water which may possibly arise during the reaction. The cyclization is preferably carried out in the presence of a catalyst, e.g. an acid such as sulphuric acid, or in the presence of carbodiimides, such as dicyclohexylcarbodiimide. The amount of acid is preferably from 5 to 20 mole %, especially from 8 to 12 mole %, the amount of carbodiimide is preferably 100 to 150 mole %, especially 100 to 120 mole %, respectively based on the number of moles of the 2-hydroxyphenyl derivative which is used.

In contrast to the named lactones, namely the unsubstituted or ring-substituted 2-coumaranones, 3,4-dihydrocoumarin or 3H-benzo-1,4-dioxin-2-ones, the other initial substances, namely the unsubstituted or ring-substituted hydroxyphenylacetic acids, hydroxyphenoxyacetic acids and hydroxyphenylpropionic acids or their derivatives contain a free hydroxyl group which should be protected before the further reaction, i.e. the (further) aromatic substitution or esterification with 3-iodo-2-propyn-1-ol or its derivatives.

The protection of the phenolic hydroxyl group, i.e. its reversible blocking, can, for example, be carried out by esterification with derivatives of $C_1$ to $C_{10}$ carboxylic acids, such as their halogenides, anhydrides, reactive esters etc. Preferred as the protective groups, and thus also as protective groups Y in formula (II), are the acetyl group and the benzoyl group. Further examples include the propionyl-, butanoyl-, isobutanoyl-, n-pentanoyl-, pivalyl-, octanoyl-, decanoyl- and o-, m-, and p-methylbenzoyl groups. In principle, however, every known protective group for hydroxyl groups can be used which is stable under reaction conditions and which can be removed again after the reaction without important undesirable side reactions.

The initial substances of formula (II) or (IV) can be transesterified or esterified with 3-iodo-2-propyn-1-ol.

The reaction with 3-ido-2-propyn-1-ol is carried out preferably at temperatures from $-10°$ C. to $+100°$ C., especially from $+20°$ to $+60°$ C. The work can be carried out at a pressure of the surrounding atmosphere, but it can also be done at higher or lower pressure. Pressures from 0.09 to 0.11 MPa (abs.) are preferred.

The reaction is preferably carried out in a solvent which is inert against the reagents. Examples of such solvents include hydrocarbons, such as benzene, toluene, xylene, petroleum ether, n-hexane, n-heptane, hexane-isomer mixture; halogen-hydrocarbons, such as dichloromethane, trichloromethane, tetrachloromethane, 1,1,1-trichloromethane, chlorobenzene, bromobenzene; ether such as diethyl ether, tetrahydrofuran and 1,4-dioxan. It is preferable that the solvent should be largely anhydrous.

The esterification or transesterification is carried out with special preference in the presence of one or more of the above named basic catalysts. The quantity of basic catalysts amounts preferably to 0.01-2 mole %, especially 0.1-0.3 mole %, based on the molecular weight of the compound of formula (II) or (IV) used.

If a compound of formula (II) has been used as the initial substance for the esterification or transesterification, subsequently the protective group which is designated with "Y" in formula (II) must be separated. This separation can, for example, be performed hydrolytically or aminolytically. The aminolysis is done preferably by reaction with ammonia, primary or secondary amines in an inert solvent, such as diethyl ether, tetrahydrofuran, dioxan, ethylene glycol dimethyl ether, toluene, xylylene and pyridine, preferably at $-10°$ to $100°$ C., especially at $20°$ to $40°$ C.

Because of their more simple method of preparation, as the inventively prepared hydroxyphenyl or hydroxyphenoxyalkanoic acid iodopropargyl esters according to the invention, compounds of the formula (V) are preferred:

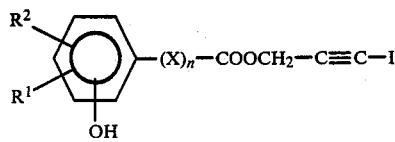

(V)

especially those of formula (VI).

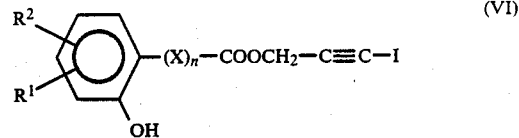

(VI)

The following examples serve to illustrate the invention. The compounds according to the invention were identified by $^1$H-NMR-spectroscopy. The substances which are identified below as commercial can be obtained from Janssen Chimica, D-4054 Nettetal 2. The reactions were carried out at approx. 1020 kPa (abs.), unless otherwise indicated.

EXAMPLE 1

4-hydroxyphenylacetic acid iodopropargyl ester (Compound 1c)

A. 20 g (0.13 mole) of 4-hydroxyphenylacetic acid (commercial) were added in a period of 10 minutes to a mixture of 40.2 g (0.39 mole) of acetic anhydride and two drops of concentrated sulphuric acid, the mixture being heated from room temperature to 45° C. After the exotherm ceased (deactivation of the exothermal reaction), stirring was carried out for a further hour at room temperature, the reaction mixture was then poured onto 500 ml 1N hydrochloric acid and extracted with 300 ml ethyl acetate, the organic phase was dried over sodium sulfate and the solvent was distilled off. The result was 26.2 g 4-acetoxyphenylacetic acid which was heated at reflux together with 31 g thionyl chloride until the end of the gas development (approx. 1 hour). The excess thionyl chloride was distilled off at a pressure of 1.6 kPa (abs). At a pressure of 27 Pa and at a temperature of 111°–112° C., 20 g (72% of the theoretical quantity) of 4-acetoxyphenylacetyl chloride were distilled over (m. p. 41°–43° C.).

B. To a solution of 12.8 g (0.071 mole) of 3-iodo-2-propyn-1-ol and 5.6 g (0.071 mole) pyridine in 30 ml anhydrous toluene, a solution of 15 g (0.071 mole) of 4-acetoxyphenylacetyl chloride (produced in accordance with A) were added at room temperature in 70 ml of anhydrous toluene. After the (deactivation of the exothermal reaction), the reaction mixture was twice washed with 1N hydrochloric acid and respectively once with saturated aqueous sodium bicarbonate solution and with water. From the organic phase, after distillation of the solvent, 23.2 g (91% of the theoretical amount) of 4-acetoxyphenylacetic acid iodopropargyl ester (m.p. 80°–85° C.) were obtained.

C. At room temperature, 15 g (0.042 mole) of 4-acetoxyphenylacetic acid iodopropargyl ester (prepared according to B) and 3.1 g (0.042 mole) of n-butylamine was stirred in 15 ml dioxan for 18 hours. The reaction mixture was distributed between diethyl ether and 1N aqueous hydrochloric acid, the ether phase was dried over sodium sulfate and the solvent mixture was distilled off. Ray yield: 14.4 g. After chromatography on silica gel with trichloromethane/petroleum ether (4:1 parts by volume) as the eluent, 8.2 g (62% of the theoretical amount) 4-hydroxyphenylacetic acid iodopropargyl ester (m.p. 73°–77° C.) were obtained.

EXAMPLE 2

2-hydroxy-5-nitrophenylacetic acid iodopropargyl ester (compound 1d)

A. 10 g (0.074 mole) of 2-coumaranone (commercial) were inserted in 14 ml of concentrated nitric acid (d=1.4) at 8° C., with strong stirring. Then 12 ml of concentrated sulphuric acid were slowly dropped in (d=1.84) at the same temperature until the clearly exothermal reaction began. Thereafter the reaction mixture was stirred with 100 g of ice and the precipitated raw nitro-coumaranone was filtered off. 11.7 g (88% of the theoretical amount) of the raw product of m.p. 173°–184° C. were obtained, and after recrystallization from ethylacetate 9.5 g of weakly yellow colored crystals of m.p. 184°–188° C. were obtained.

B. A mixture of 4.0 g (0.022 mole) of 5-nitrocoumaranone, 4.0 g (0.022 mole) 3-iodo-propyn-1-ol, 50 mg 4-dimethylaminopyridine was stirred in 22 ml of anhydrous toluene at room temperature for 22 hours. The resultant deposit was filtered off, washed with a little toluene and 4.5 g (57% of the theoretical amount) of 2-hydroxy-5-nitrophenylacetic acid iodopropargyl ester (m.p. 145°–149° C.) were obtained.

EXAMPLE 3

(2-hydroxy-3,5-dinitrophenoxy)acetic acid iodopropargyl ester (compound 2c)

A. To a solution of 110.3 g (1.00 mole) catechol (commercial) and 79.0 g (1.00 mole) of pyridine in 250 ml anhydrous diethyl ether, 112.9 g (1.00 mole) chloroacetyl chloride dissolved in 80 ml anhydrous diethyl ether were slowly added, while stirring at a temperature of from 25° to 35° C. After the end of the reaction, the work is done as follows:

The mixture is extracted with 1N hydrochloric acid, then is dried over sodium sulfate and the solvent is distilled off. 169.8 g (91% of the theoretical amount) of raw chloroacetic acid 2-hydroxyphenyl ester are obtained with a melting point of 32°–35° C.

B. 161.5 g (0.87 mole) of chloroacetic acid 2-hydroxyphenyl ester were dissolved in 300 ml of anhydrous dimethylformamide. 20.88 g (0.87 mole) of sodium hydride were added portion by portion with indirect ice refrigeration. After the ending of the addition, heating was carried out for 3 hours at 35° C. followed by hydrolysis in which the reaction mixture was distributed between 600 ml 1N hydrochloric acid and 600 ml diethyl ether. The organic phase was dried with sodium sulfate and was concentrated by evaporation. 117.6 g (90% of the theoretical amount) of raw 3-H-benzo-1,4-dioxin-2-one were obtained. The light-brown oil which was accumulated at first was crystallized in the course of time (melting point 45°–53° C.²).

C. For nitration, 25 g (0.167 mole) of 3-H-benzo-1,4-dioxin-2-one were added to 87.7 g (0.835 mole) of 60 percent nitric acid. By cooling, the reaction temperature was kept between 10° and 15° C. After the ending of the addition, stirring was carried out at the same temperature for a further three hours and then the reaction mixture was poured onto 500 g of ice. The result was 31 g of a solid which is insoluble in water from which after successive treatment with 2N sodium hydroxide solution, 1N acetic acid as well as water, 25.8 g (60% of the theoretical amount) of (2-hydroxy-3,5-dinitrophenoxy)acetic acid were obtained with a melting point of 148°–153° C.

D. To a solution of 25.8 g (0.100 mole) of (2-hydroxy-3,5-dinitrophenoxy) acetic acid in 140 ml of anhydrous acetone, was added a solution of 24.7 g (0.120 mole) of dicyclohexylcarbodiimide in 70 ml of anhydrous acetone at room temperature.

After 1 hour the precipitated dicyclohexylurea was filtered off and the filtrate was concentrated by evaporation. The residue, 6,8-di-nitro-3-H-benzo-1,4-dioxin-2-one, was dissolved in 70 ml of anhydrous dioxan, 18.3 g (0.100 mole) of 3-iodopropyn-1-ol dissolved in 30 ml of anhydrous dioxan as well as 20 mg 4-dimethylaminopyridine were added, and this reaction mixture was stirred at room temperature for 15 hours. For workup, the reaction mixture was distributed between 500 ml of ethyl acetate and 500 ml of 1N hydrochloric acid. After drying and concentration by evaporation of the organic phase, 52.0 g of the raw product are obtained, from which by recrystallization in ethyl acetate, 27.1 g (64% of the theoretical amount) of pure (2-hydroxy-3,5-dinitrophenoxy)acetic acid iodopropargyl ester were obtained with a melting point of 134° to 136° C.

In the following examples, the biological effectiveness was tested of the following compounds:

(1) Compounds according to the invention

TABLE I $R^2$, $R^1$, OH — $(X)_n$ — $COOCH_2$ — $C\equiv C$ — I (V)

| Compound No. | Meaning of $(X)_n$ | Position of OH—group | Position and Meaning of $R^1$ | of $R^2$ | See Example Number |
|---|---|---|---|---|---|
| 1 b | $CH_2$ | 3 | H | H | — |
| 1 c | " | 4 | H | H | 1 |
| 1 d | " | 2 | 5-$NO_2$ | H | 2 |
| 1 e | " | 2 | 5-Cl | H | — |
| 2 a | $O-CH_2$ | 2 | H | H | — |
| 2 c | " | 2 | 3-$NO_2$ | 5-$NO_2$ | 3 |
| 3 a | $CH_2-CH_2$ | 2 | H | H | — |
| 3 b | " | 2 | 3-$NO_2$ | H | — |
| 3 c | " | 2 | 5-$NO_2$ | H | — |
| 3 d | " | 2 | 5-Cl | H | — |
| 3 e | " | 2 | 3-$NO_2$ | 5-$NO_2$ | — |

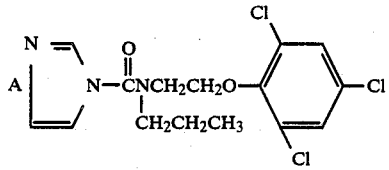

Prochloraz$^R$ (Fm. FBC/Schering)

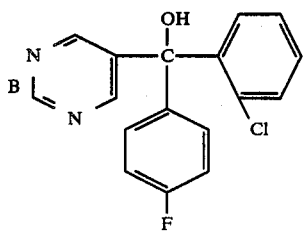

Nuarimol$^R$ (Fm. Eli-Lilly)

TABLE I-continued $$\underset{\underset{OH}{R^1}}{\overset{R^2}{\bigcirc}}-(X)_n-COOCH_2-C\equiv C-I \quad (V)$$

| Compound No. | Meaning of $(X)_n$ | Position of OH—group | Position and Meaning of $R^1$ | of $R^2$ | See Example Number |
|---|---|---|---|---|---|

Vinclozolin ® (Fm. BASF)
[structure: CH₃C with O, O, N attached to dichlorophenyl ring]

D  ClCH₂COOCH₂C≡C—I
Compound 32 of U.S. Pat. No. 4,259,350

E  [naphthalene]—CH₂COOCH₂C≡C—I

F  [CH₃C(O)CH₂C(O)]OCH₂C≡C—I

G  [2,6-dichloro-4-nitrophenyl]—CH₂COOCH₂C≡C—I
EP-A 160 962 Example 3

H  [phenyl]—CH₂COOCH₂C≡C—I
Compound 60 of U.S. Pat. No. 4,259,350

The compounds according to the invention have fungicide effectiveness and are suitable for combating fungoid infestation of plants and plant products.

The active ingredients described above are distinguished by a broad spectrum of effects and are suitable, in particular, for combating types of alternaria, *Botrytis cinerea*, types of fusarium, *Colletortrichum coffeanum, Verticillium dahliae, Penicillium glaucum* and diverse rubiginous fungi.

The inventive substances are suitable, for example, for use in vineyards, in vegetable and flower growing, in agricultural crops as well as in growing fruit, particularly for strawberry plantations, without their field of application being limited to the above. A further field of application has been found in their use as seed caustic agents for combating seed-growing pathogens.

The active ingredients according to the invention can be produced either by themselves or in a mixture with other pesticides and, in particular, fungicidal agents. In this respect mixtures with known fungicides, the use of which in practice is restricted because of the progressive development of resistant strains of fungi in the meanwhile, must be stressed.

In general the active ingredients according to the invention are used as mixtures with solid or liquid diluents or as solutions in solid or liquid solvents with contents of the active ingredient ranging from 0.01 to 95% by weight.

The mixtures or solutions are produced, for example, as emulsifiable concentrates, pastes, wettable powders, granulates or microcapsules.

Emulsifiable concentrates and pastes contain in general from 10 to 90% by weight, preferably from 15 to 50% by weight, of the active ingredient, from 1 to 25% by weight of a dispersing agent and organic solvents and/or water.

Wettable powders usually contain 10 to 80% by weight, preferably 15 to 70% by weight of the active ingredient, 1 to 20% by weight of the dispersing agent and from 10 to 89% by weight of inert components.

Granulates and powdery agents contain apart from the inert components, bonding agents and/or coating substances, from 1 to 10% by weight, particularly from 5 to 10% by weight, of active ingredient.

According to the invention the following adjuvants may also be used:

Useful dispersing agents include, for example, alkyl and aryl sulfonates, methyl cellulose, polymer sulfonic acids and their salts, polyalcohols, fatty acid esters, fatty alcohol ethers, fatty amines, and lignin sulfonate. Useful organic solvents include, for example, alcohols, such as ethanol, butanol; dimethylformamide, dimethylsulfoxide, N-methylpyrrolidone; and aromatics, such as toluene and xylenes.

Inert components which may be employed include, for example, porcelain clay, china clay, talc, calcium carbonate, highly dispersed silicic acid, silicic gel, kieselghur, diatomaceous earth, pumice, maize chips, thickening agents such as starch and carboxylmethyl cellulose.

Bonding agents which may be used include, for example, magnesium sulfate, gypsum and gum arabic.

The active ingredients according to the invention may be formulated as shown in the following examples.

1. Emulsifiable concentrate:
   20% by weight active ingredient
   10% by weight expoxylated anhydrosorbitanmonolaurate available on the market (trade name "Tween-Twenty", manufacturer: Atlas Chemie, D-4300 Essen)
   70% by weight dimethylformamide 2. Wettable powders:
   20% by weight of active ingredients,
   5% by weight ammonium lignin sulfonate, type ALN 4, manufacturer: Dille, D-2000 Norderstedt
   10% by weight sodium oleylmethyltauride (trade name "Arcopon T. KONZ", manufacturer: Hoeschst AG, D-600 Frankfurt)
   65% by weight porcelain clay.

The quantities of the active ingredients which are used can vary within large ranges. In general when treating seeds, amounts of active ingredient of from 0.05 to 25 g/kg of seed are required.

However, the application of the active ingredients according to the invention can be carried out in any suitable form. For example, pouring, spraying, injection, atomization, painting and caustic treatment of the seed.

EXAMPLE 4

Spore germ test:

50 μl of a solution or suspension of an inventive active ingredient were produced together with 50 μl of a spore suspension by floating off the spores from an agricultural crop with a nutrient solution which contains per 1 10 g of sugar, 1 g glycol, 1 g KH₂PO₄ and 0.5 g MgSO₄, and were inserted in the concave edge object carriers. The object carriers were cultivated at 20° C. in a closed Petri dish, the base of which was covered with moistened filter paper, for 48 hours. Subsequently the ratio of the germinated to the nongerminated spores was compared against an untreated control sample. The degree of effectiveness was computed in percent by using the following formula:

$$1 - \frac{\text{number of germinated spores treated}}{\text{number of germinated spores untreated}} \times 100$$

The results are shown in the following Table 2.

TABLE 2

Percent of germ prevention in the case of spores of fungi, concentration of active ingredient 31 ppm

|  | I | II | III | IV | V | VI | VII |
|---|---|---|---|---|---|---|---|
| Active Ingredient |  |  |  |  |  |  |  |
| 1 b | 100 | 90 | 100 | 100 | 100 | 100 | 90 |
| 1 d | 100 | 100 | 100 | 100 | 100 | 100 | 100 |
| 2 a | 20 | 30 | 50 | 80 | 100 | 90 | 40 |
| 2 c | 100 | 70 | 100 | 100 | 100 | 100 | 100 |
| 3 a | 100 | 100 | 100 | 90 | 100 | 100 | 100 |
| 3 d | 100 | 100 | 100 | 100 | 100 | 100 | 100 |
| 3 e | 100 | 100 | 80 | 100 | 100 | 90 | 80 |
| Comparative Agent |  |  |  |  |  |  |  |
| A | 40 | 70 | 10 | 20 | 0 | 10 | 100 |
| B | 0 | 70 | 0 | 90 | 20 | 80 | 50 |

I = *Alternaria alternata*
II = *Botrytis cinerea*
III = *Fusarium culmorum*
IV = *Fusarium nivale*
V = *Colletotrichum coffeanum*
VII = *Penicillium glaucum*

EXAMPLE 5

Combating uromyces fabae, bean rust:

Bean plants grown to a height of 10 cm were sprayed to be dripping wet with a spray mixture which had 500 or 125 ppm concentration of the active ingredient. 24 hours after this treatment the inoculation of the plants was carried out with spores of *Uromyces fabae* by spraying with a spore suspension which contained approximately $5 \times 10^4$ spores per ml.

Subsequent to the inoculation, the plants were placed for 24 hours in a dark humid room at a temperature of 17° C. and a relative air humidity of 95%. Thereafter the plants were brought into the greenhouse and after a further 10 days were evaluated by means of a value scale for infestation.

The infestation values which were obtained are an expression of the level of efficiency of the agent according to the invention against fungus rust.

| Infested leaf area in % | Effectiveness in % |
|---|---|
| 0 | 100 |
| up to 3 | 80 |
| up to 10 | 60 |
| up to 25 | 40 |
| up to 50 | 20 |
| more than 50 | 0 |

TABLE 3

Efficiency in % against *uromyces fabae* in horse beans at active ingredient concentrations of

| Active ingredient | 500 ppm | 125 ppm |
|---|---|---|
| 1 b | 100 | 90 |
| 1 c | 100 | 80 |
| 1 d | 100 | 90 |
| 1 e | 100 | 70 |
| 2 a | 100 | 90 |
| 2 c | 100 | 90 |
| 3 b | 100 | 95 |
| 3 c | 100 | 90 |
| 3 d | 90 | 30 |
| 3 e | 90 | 80 |
| Comparative Agent |  |  |
| A | 70 | 20 |
| B | 100 | 50 |
| C | 40 | 20 |
| D | 0 | 0 |
| E | 50 | 0 |
| F | 40 | 0 |
| G | 60 | 10 |
| H | 90 | 40 |

EXAMPLE 6

Combating *Fusarium nivale* (caustic agent test):

Rye seed infested naturally with *Fusarium nivale* was corroded with the active ingredients formulated as dry caustic agents in a quantity of 500 ppm evenly. After the corrosion, the rye grains were placed in dishes with sterilized and humid brick dust. The dishes were firstly placed in darkness at 13° C. in the refrigerator. After the emergence of the seeds, after 6 days, further cultivation was carried out for a further 7 days with artificial illumination in the refrigerator.

Then the plants were investigated for infestation symptoms by *Fusarium nivale*.

Untreated controls were used for comparison. The degree of efficiency in percent was found according to the following formula:

$$\% = \frac{U\% - B\%}{U\%} \times 100$$

U% = infestation percentage in the case of untreated samples;
B% = infestation percentage in the case of treated samples.

The results are shown in the following Table 4.

TABLE 4

Efficiency in % at 500 ppm active ingredient compensation against *fusarium nivale* (snow mould)

| Active ingredient |  |
|---|---|
| 1 b | 90 |
| 1 c | 60 |
| 1 d | 100 |
| 2 a | 100 |
| 2 c | 90 |
| 3 a | 80 |
| 3 b | 100 |
| 3 c | 90 |
| 3 d | 80 |
| 3 e | 85 |
| Comparative Agent |  |
| A | 70 |
| B | 70 |
| D | 20 |
| E | 30 |
| F | 30 |

TABLE 4-continued

Efficiency in % at 500 ppm active ingredient compensation against *fusarium nivale* (snow mould)

| | |
|---|---|
| G | 90 |

EXAMPLE 7

Combating botrytis cinerea, grey mould:

Hybrid fuchsia of the type "Ortenburger Festival" were cultivated in the greenhouse at temperatures from 18° to 25° C. and a relative air humidity of 75%, until they reached an average height of 10 cm. The plants were then injected until they dripped with the active substances formulated as an injection powder. Twenty-four hours after treatment artificial inoculation was carried out with the conidia of the fungus *Botrytis cinerea* (spore density: approx. $5 \times 10^4$/ml of spore germ solution). To improve the conditions for the pathogen, during the entire duration of the test care was taken to achieve even moistening of the leaves and high air humidity at 95% (by covering with polyethylene film). Fourteen days after the treatment, the plants were evaluated in accordance with an evaluation code used by the Biologische Bundesanstalt from 1 to 9 (1=no infestation, 9=total infestation) for infestation symptoms.

The calculation of the degree of efficiency was carried out in accordance with the following formula:

$$Ef\% = \frac{\%\ \text{infestation in control} - \%\ \text{infestation in test}}{\%\ \text{infestation in control}} \times 100$$

The values which were obtained are reflected in Table 5.

TABLE 5

Efficiency in % at 500 ppm active ingredient concentration against *botrytis cinerea* (grey mould)

| Active ingredient | Average value from 10 Test plants resp. |
|---|---|
| 1 b | 78 |
| 1 c | 76 |
| 1 d | 95 |
| 1 e | 43 |
| 2 a | 81 |
| 2 c | 93 |
| 3 b | 80 |
| 3 c | 86 |
| 3 d | 93 |
| 3 e | 90 |
| Comparative Agent | |
| C | 62 |
| D | 43 |
| E | 43 |
| F | 0 |
| G | 0 |

TABLE 5-continued

Efficiency in % at 500 ppm active ingredient concentration against *botrytis cinerea* (grey mould)

| | Average value from 10 Test plants resp. |
|---|---|
| H | 0 |

In Example 7 the high effectiveness of the claimed substances according to the invention against botrytis cinerea is impressively documented. The relatively weak degree of effectiveness of the special botryticide Comparative Agent C indicates the extraordinary massive infection conditions of the test.

What is claimed is:

1. Compounds having the formula

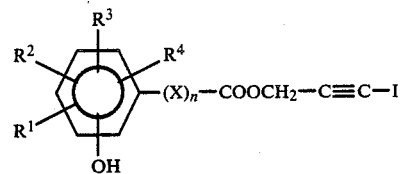

wherein $R^1$, $R^2$, $R^3$, $R^4$ may be identical or different radicals in any desired position on the benzene ring, namely fluoro, chloro, bromo, iodo, cyano, or nitro radicals, alkyl radicals having from 1 to 4 carbon atoms, cyclo alkyl radicals having from 3 to 7 carbon atoms, phenyl, phenyl sulfonyl and phenoxy radicals and hydrogen;

n can be a number with the value of 1 or 2 and x can be $CH_2$ and, where n=1, $O-CH_2$ as well.

2. Compound of claim 1 wherein $R^3$ and $R^4$ are hydrogen.

3. Compound of claim 1 having the formula

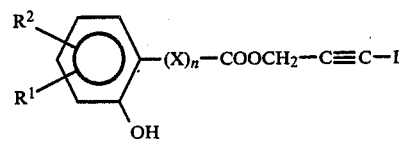

where $R^1$, $R^2$, X and n have the meanings given in claim 1.

4. Compound of claim 2 wherein $R^1$ and $R^2$ are hydrogen, OH is in the 3-position, X is $CH_2$ and n is 1.

5. Compound of claim 3 wherein $R^1$ is 5-$NO_2$, $R^2$ is H, X is $CH_2$ and n is 1.

6. Compound of claim 3 wherein $R^1$ is 5-Cl, $R^2$ is H, X is $CH_2$ and n is 2.

7. Composition comprising an inert carrier and a fungicidally effective amount of a compound of any one of claims 1 to 6.

8. Method for controlling fungi which comprises applying a composition in accordance with claim 7 to a substrate to be protected.

* * * * *